US007458931B2

(12) United States Patent
Cassou

(10) Patent No.: US 7,458,931 B2
(45) Date of Patent: Dec. 2, 2008

(54) SYRINGE FOR ARTIFICIAL INSEMINATION WITH LATERAL WINDOW

(75) Inventor: Bertrand Cassou, Saint Symphorien des Bruyeres (FR)

(73) Assignee: IMV Technologies, L'Aigle (FR)

(*) Notice: Subject to any disclaimer, the term of this patent is extended or adjusted under 35 U.S.C. 154(b) by 325 days.

(21) Appl. No.: 10/497,465

(22) PCT Filed: Dec. 3, 2002

(86) PCT No.: PCT/FR02/04146

§ 371 (c)(1),
(2), (4) Date: Jan. 6, 2005

(87) PCT Pub. No.: WO03/047458

PCT Pub. Date: Jun. 12, 2003

(65) Prior Publication Data

US 2005/0107659 A1 May 19, 2005

(30) Foreign Application Priority Data

Dec. 4, 2001 (FR) .................................. 01 15642

(51) Int. Cl.
*A61B 17/43* (2006.01)

(52) U.S. Cl. ........................................................ 600/34

(58) Field of Classification Search ..................... 600/3, 600/7, 33–35; 222/460, 461, 546, 554, 562; 604/48, 57, 61, 93.01, 500, 514, 515; 606/126
See application file for complete search history.

(56) References Cited

U.S. PATENT DOCUMENTS

| | | | | |
|---|---|---|---|---|
| 2,705,956 | A | 4/1955 | McLaughlin | |
| 3,507,281 | A | 4/1970 | Cassou | |
| 4,173,227 | A * | 11/1979 | Cassou et al. | 604/218 |
| 4,493,700 | A * | 1/1985 | Cassou et al. | 600/35 |
| 6,010,446 | A * | 1/2000 | Grimm | 600/3 |
| 6,207,671 | B1 | 3/2001 | Schmidt et al. | |
| 6,402,677 | B1 * | 6/2002 | Jacobs | 600/7 |
| 6,572,525 | B1 * | 6/2003 | Yoshizumi | 600/7 |
| 6,586,613 | B1 | 7/2003 | Brandes et al. | |

FOREIGN PATENT DOCUMENTS

| | | |
|---|---|---|
| EP | 0 416 975 | 3/1991 |
| EP | 0818448 | 1/1998 |
| WO | 9914174 | 3/1999 |

* cited by examiner

*Primary Examiner*—Samuel G Gilbert
(74) *Attorney, Agent, or Firm*—Young & Thompson

(57) ABSTRACT

The invention concerns a syringe for injecting the content of a straw enabling the reading of data borne by the straw, even when it is ready for use. The straw is placed in a tubular body (12) of the syringe in a housing (30) wherein is provided at least a lateral window (38).

10 Claims, 2 Drawing Sheets

SYRINGE FOR ARTIFICIAL INSEMINATION WITH LATERAL WINDOW

Figure 1:
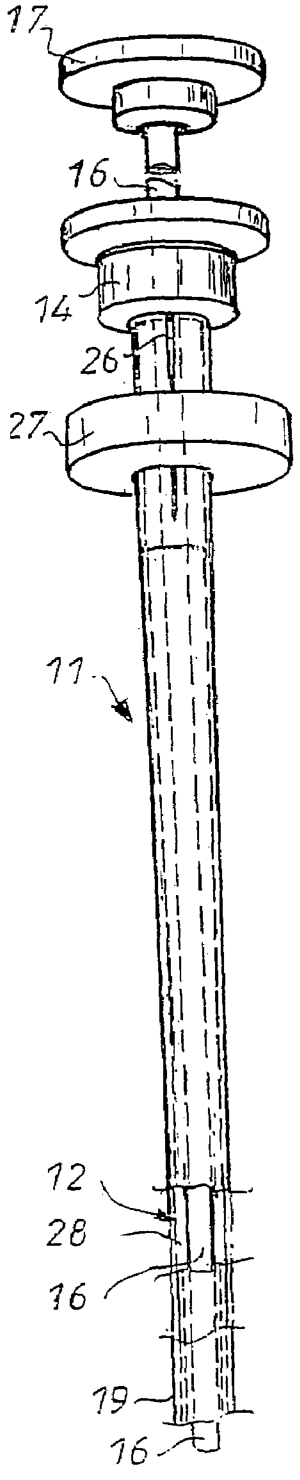

The invention concerns a syringe for injecting the contents of a straw for the artificial insemination of an animal. It has the more particular object of an improvement enabling the reading of information on the straw even when it is inside the syringe, ready for use.

Insemination syringes of the above kind are used for the artificial insemination of livestock, in particular cattle, sheep, goats, rabbits.

An insemination syringe intended to receive a straw for depositing gametes or for embryo transfer, in particular in animals, usually called a "Cassou pistol", comprises a rigid tubular body, defining the chamber of the pistol, intended to receive a straw filled with semen, and a piston mounted to slide in said tubular body. A transparent material flexible sanitary sheath encloses the tubular body, and is intended for single use, for example. It is fixed removably around the tubular body. The tubular body and the piston are reusable. They must have a certain stiffness and mechanical strength. This is why they are generally made of metal, preferably of stainless steel. For this reason, the tubular body is opaque.

Moreover, the straw carries inscriptions for precisely identifying the semen of the requested sire. For example, in the case of bull semen, the name of the sire bull, the livestock references, the breed of the bull, and the place and the date of obtaining the semen are usually inscribed on the straw. A bar code for automatic reading of this information may be carried by the straw.

With a syringe of the kind indicated hereinabove, the inseminator may no longer be able to read the inscriptions or the bar code on the straw when it is inserted into the tubular body of the injection syringe. Now, it may be desirable to prepare a plurality of syringes at the same time before carrying out the first insemination. There is therefore a risk of mixing up the selected sire, to be used for a given female, from a herd of the same breed.

The invention enables an inseminator using an injection syringe for straws to read the inscriptions and the reference on a straw of this kind even when it is inserted into the tubular body, ready for use.

The invention more particularly concerns a syringe for injecting the contents of a straw for the artificial insemination of an animal or for embryo transfer, comprising a tubular body intended to receive a straw of this kind, said body having an opening at its distal end, a piston sliding in said body, and a transparent sanitary sheath fitting over the outside of said tubular body, characterized in that said tubular body comprises at least one lateral notch formed at a location allowing reading of information carried by a straw when the latter is inserted and located in a housing defined in said tubular body.

There may be a single lateral notch. Its width is preferably less than the diameter of the straw, i.e. the diameter of the tubular body or at least the portion thereof that is intended to receive the straw. This avoids bending of the straw during transfer, which assures a smooth injection, with the straw correctly aligned with the piston. This notch has an elongate shape. It may extend over almost all of the section of the tubular body that is intended to receive the straw, although not including the two ends of this section and in particular that which is located near the opening of said tubular body.

In a manner that is known in the art, the tubular body includes a piston guiding portion that is extended in the axial direction by a larger diameter housing for the straw. This housing is therefore connected to the piston guiding portion by a shoulder that forms a locating abutment for the straw. In this case, the notch extends along said housing, than which it is shorter, without reaching either the shoulder or said distal end.

The sanitary sheath is made from a flexible transparent thermoplastic material. From the optical point of view, it forms a kind of magnifying glass that makes it easier to see the inscriptions carried by the straw when the latter is in its housing.

The tubular body and the piston are made of metal and preferably of stainless steel.

With an injection syringe of the above kind, the inscriptions and/or the bar code carried by the straw may be read until the last moment, even when the syringe is ready for use. Paternity errors are therefore no longer possible.

Figure 2:
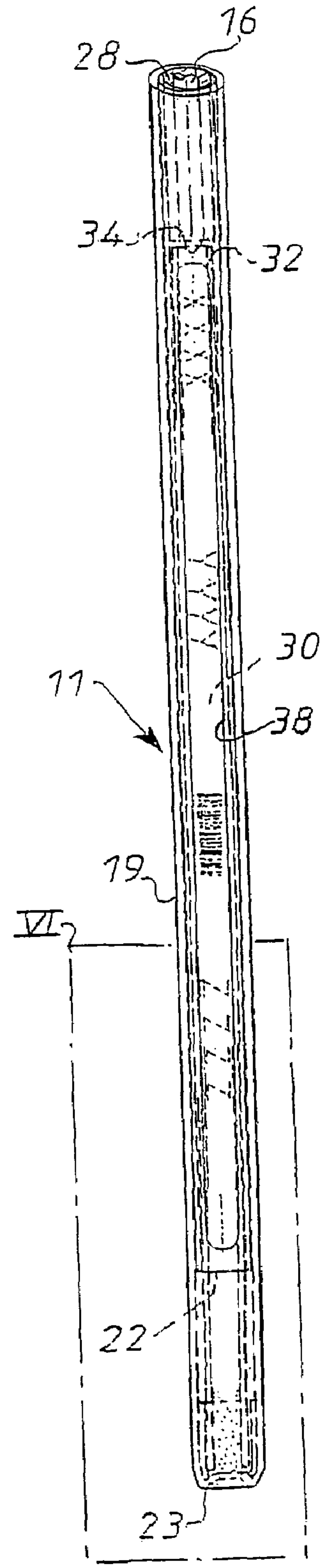
Figure 6:
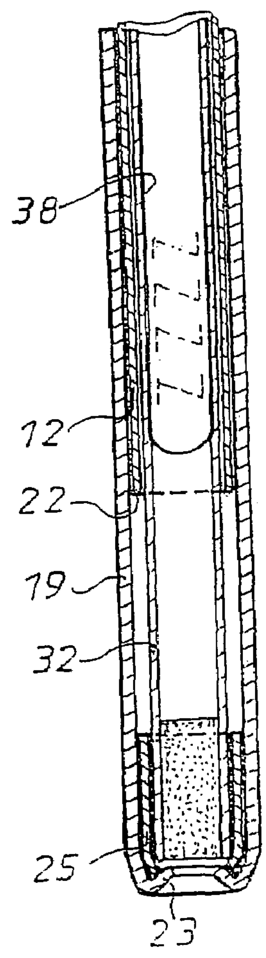
Figure 4:
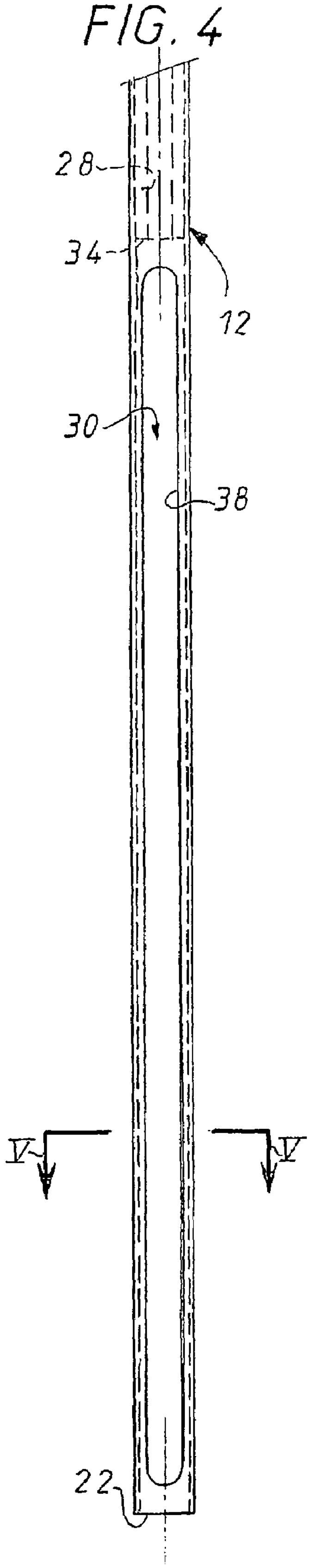
Figure 3:
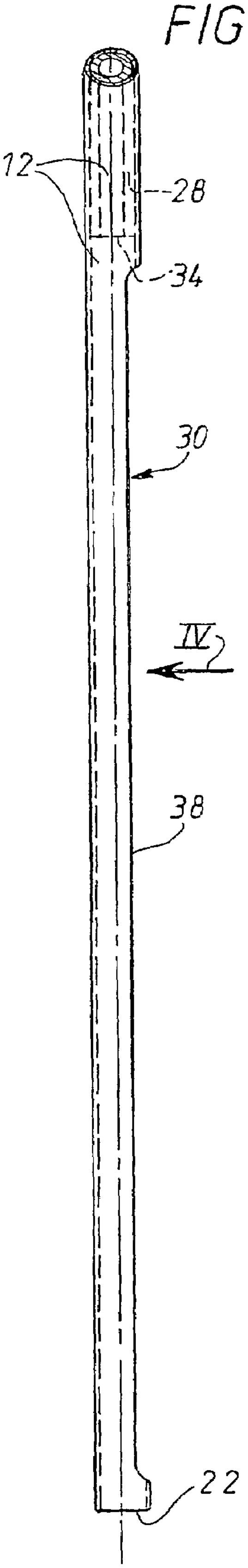
Figure 5:
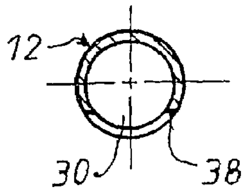

The invention will be better understood and other advantages of the invention will become more clearly apparent in the light of the following description of one preferred embodiment of an injection syringe conforming to the invention, which is given by way of example only and with reference to the appended drawings, in which:

- FIG. 1 is a cut-away partial perspective view of the proximal portion of the syringe, i.e. the portion at the end with the operating pushbutton, the sanitary sheath being fitted;
- FIG. 2 is a partial view of the distal portion of the same syringe, with the sheath fitted and the straw in place in its housing;
- FIG. 3 is an elevation view of the distal portion of the tubular body of the syringe;
- FIG. 4 is a view in the direction of the arrow IV in FIG. 3;
- FIG. 5 is a view in section taken along the line V-V in FIG. 4; and
- FIG. 6 is a view in section to a larger scale of the portion inside the box V in FIG. 2.

The injection syringe 11 according to the invention comprises a rigid tubular body 12 provided with a ring 14 at a proximal end and with a piston 16 essentially taking the form of a simple rod terminated by a pushbutton 17 fixed to the proximal end of said piston. By "proximal end" is meant the end of the device that is manipulated by the inseminator during the operation; the distal end is that which is inserted into the vaginal orifice of the animal. The components described hereinabove are reusable. They are preferably made of metal, for example of stainless steel. A portion intended for single use consists of a transparent thermoplastic material sanitary sheath 19 that fits over the tubular body. The latter has an opening 22 at its distal end and the sheath has an opening 23 at its distal end which is aligned with the opening 22 of the tubular body. The opening 23 of the sanitary sheath 19 is defined by a hemmed internal edge of the distal end of the latter. A plastic material sliding sleeve 25 is inserted into the sheath. When said sheath is fitted over the tubular body of the syringe, this sleeve is pushed to the end 23 so that it is immobilized in the extension of the rolled internal edge.

The exterior wall of the tubular body 12 in the immediate vicinity of the ring 14 has a portion of increased thickness that is substantially conical. The proximal end portion of the sheath 19 is slit (slit 26) to cover this conical portion. A plastic material locking ring 27 slides along the wall of the tubular body until it clamps the sheath 19 onto the conical portion. This plastic material ring is of a predetermined color that corresponds to the breed of the animal.

The tubular body 12 comprises two portions, namely a small diameter portion 28 for guiding the piston 16 and a larger diameter housing 30 for a straw 23 axially extending the guiding portion 28. Consequently, said guiding portion 28 extends between an orifice leading to the center of the ring 14 and an internal shoulder 34 of the tubular body whereas the larger diameter housing for the straw extends between the shoulder 34 and the opening 22 defined at the distal end of said tubular body. This shoulder 34 forms a locating abutment for the straw 32.

The tubular body 12 has at least one lateral notch 38 formed at a location enabling information carried by the straw to be read when the straw is inserted and positioned at a predetermined location in said tubular body, i.e. in its housing 30 defined between the shoulder 34 and the opening 22. In the example, there is a single notch 38 that extends over almost all of the housing 30 for the straw but without reaching either the distal end of the body or the shoulder 34. When the straw 32 is in position in its housing, it extends a little way beyond the opening 22.

As FIGS. 3 to 5 show, the width of the lateral notch 38 is less than the diameter of the tubular body in the portion where the latter is conformed and sized to receive the straw. In the example shown, there is only one lateral notch 38. It is of elongate shape and constant length and is rounded at its ends.

A syringe according to the invention is used in the following manner. The operator withdraws the piston 16 to expose the housing 30 of the straw. After opening both ends of the straw, he introduces it into the housing 30 of the tubular body through the opening provided for this purpose, until one end of the straw bears against the shoulder 34. He then fits the sanitary sheath 19 over the tubular body, sliding it on from the distal end thereof. This has the effect of progressively pushing back the sleeve 25 until it abuts in line with the hemmed edge at the end 23 of the sheath. During this same operation, the end of the straw 32 is engaged in the sleeve 25 and is therefore clamped to the end of the sleeve. The latter thus forms a seal preventing infiltration of seminal fluid between the straw and the sleeve during the insemination operation.

Upon inserting the straw, the operator checks that the inscriptions on it are visible through the notch 38. For example, the inscriptions XXX may indicate the location of the livestock, the inscriptions YYY the date the semen was obtained, and the inscriptions ZZZ the name of the sire. A bar code representing the same information may also be printed on the straw, for automated data capture.

As soon as the straw is correctly positioned and the operations of fitting the sheath have been completed, it remains only to insert the piston 16 into the tubular body through its proximal end and the injection syringe is ready for use. The inseminator may conveniently prepare a plurality of syringes in this way before carrying out the corresponding inseminations. Errors in the choice of sire are no longer possible.

The invention claimed is:

1. A syringe for injecting the contents of a straw for the artificial insemination of an animal or for embryo transfer, comprising a tubular body (12) intended to receive a straw of this kind, said body having an opening (22) at its distal end, a piston (16) sliding in said body, and a transparent sanitary sheath (19) fitting over the outside of said tubular body, characterized in that said tubular body comprises at least one lateral notch (38) formed at a location allowing reading of information carried by a straw when the latter is inserted and located in a housing (30) defined in said tubular body, said tubular body (12) has a portion (28) for guiding the piston extended axially by said larger diameter housing (30) for said straw, this housing being connected to said guiding portion by a shoulder (34) forming a locating abutment for said straw, in that said notch (38) extends along said housing, and in that it is shorter than the latter, without reaching either said shoulder (34) or said opening (22) at the distal end of said body.

2. The syringe according to claim 1, characterized in that the width of a lateral notch (38) of this kind is less than the diameter of said housing (30).

3. The syringe according to claim 2, characterized in that said lateral notch (38) has an elongate shape of constant width.

4. The syringe according to claim 1, characterized in that said lateral notch (38) has an elongate shape of constant width.

5. Syringe according to claim 1, characterized in that said sanitary sheath (19) is made of a transparent thermoplastic material.

6. Syringe according to claim 1, characterized in that said tubular body is made of metal.

7. Syringe according to claim 6, characterized in that its metal components are made of stainless steel.

8. Syringe according to claim 1, characterized in that said piston (16) essentially comprises a metal rod terminated by a pushbutton (17).

9. Syringe according claim 8, characterized in that its metal components are made of stainless steel.

10. A syringe for injecting the contents of a straw for the artificial insemination of an animal or for embryo transfer, comprising a tubular body (12) intended to receive a straw of this kind, said body having an opening (22) at its distal end, a piston (16) sliding in said body, and a transparent sanitary sheath (19) fitting over the outside of said body, said sheath having an opening (23) at its distal end defined by a hemmed, rolled internal edge which is aligned with said opening of said body, characterized in said tubular body comprises at least one lateral notch (38) formed at a location allowing reading of information carried by a straw when the latter is inserted and located in a housing (30) defined in said tubular body, said tubular body (12) has a portion (28) for guiding the piston extended axially by said larger diameter housing (30) for said straw, this housing being connected to said guiding portion by a shoulder (34) forming a locating abutment for said straw, in that said notch (38) extends along said housing, and in that it is shorter than the latter, without reaching either said shoulder (34) or said opening (22) at the distal end of said body.

* * * * *